United States Patent
Khosla et al.

(10) Patent No.: US 6,750,047 B2
(45) Date of Patent: Jun. 15, 2004

(54) FERMENTATION AND PURIFICATION OF MIGRASTATIN AND ANALOG

(75) Inventors: Chaitan Khosla, Palo Alto, CA (US); Peter Licari, Fremont, CA (US); John Carney, San Bruno, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 182 days.

(21) Appl. No.: 09/932,167

(22) Filed: Aug. 17, 2001

(65) Prior Publication Data

US 2002/0119937 A1 Aug. 29, 2002

Related U.S. Application Data

(60) Provisional application No. 60/226,595, filed on Aug. 21, 2000.

(51) Int. Cl.[7] .................................................. C12P 17/18
(52) U.S. Cl. ........................ 435/119; 435/117; 435/118; 435/244
(58) Field of Search ................................ 435/119, 117, 435/118, 244

(56) References Cited

U.S. PATENT DOCUMENTS

| 4,916,138 A | 4/1990 | Ueda et al. | 514/294 |
| 5,484,799 A | 1/1996 | Hochlowski et al. | 514/345 |
| 5,589,485 A | 12/1996 | Hochlowski et al. | 514/315 |

FOREIGN PATENT DOCUMENTS

| EP | 423 714 | 6/1994 |
| EP | 428 169 | 3/1995 |

OTHER PUBLICATIONS

Hochlowski et al., J. Antibiotics (1994) 47:870–874.
Hondo et al., Transplantation Proceedings XIX (1987) Supp.6:17–22.
Jarvis et al., J. Antibiotics (1990) 43:1502–1504.
Kadam and McAlpine, J. Antibiotics (1994) 47:875–880.
Karwowski et al., J. Antibiotics (1994) 47:862–869.
Marshall et al. J. Industrial Microbiology (1990) 5:283–288.
Nakae et al., J. Antibiotics (2000) 53:1130–1136.
Nakae et al., J. Antibiotics (2000) 53:1228–1230.
Warr et al., J. Antibiotics (1996) 49:234–240.
Woodhouse et al., Cancer (1997) 80:1529–1537.

*Primary Examiner*—Irene Marx
(74) *Attorney, Agent, or Firm*—Morrison & Foerster LLP

(57) ABSTRACT

Migrastatin and a migrastatin analog can be produced by fermentation of *Streptomyces platensis* NRRL 18993 and used in pharmaceutical formulations to treat cancer and/or inhibit metastasis of cancer cells.

10 Claims, No Drawings

FERMENTATION AND PURIFICATION OF MIGRASTATIN AND ANALOG

CROSS-REFERENCE TO RELATED APPLICATION

This application is entitled to the benefit of the filing date of Aug. 21, 2000, for U.S. Provisional patent application Serial No. 60/226,595, entitled FERMENTATION AND PURIFICATION OF MIGRASTATIN, incorporated herein by reference.

FIELD OF THE INVENTION

The present invention provides methods for preparing migrastatin and a migrastatin analog by fermentation and migrastatin compounds useful in the treatment of disease conditions. The invention relates to the fields of chemistry, molecular biology, animal and human health sciences, and medicine.

BACKGROUND OF THE INVENTION

Migrastatin is a polyketide that inhibits the migration or movement of cells. Migrastatin has therapeutic potential in the treatment of cancer, because migrastatin can be administered, alone or in combination with other anti-cancer drugs, to prevent metastases. Unfortunately, migrastatin is quite difficult to synthesize de novo, and strains that produce the compound have heretofore either not been available or have not been identified as producers of migrastatin. There remains a need for efficient means to produce migrastatin and migrastatin analogs. The present invention meets this need.

SUMMARY OF THE INVENTION

The present invention provides methods for making migrastatin, migrastatin analogs, and purified preparations of migrastatin and migrastatin analogs. The present invention also provides compositions containing migrastatin or migrastatin analogs useful in the treatment of cancer and other disease conditions in which the inhibition of cell migration is beneficial.

In a first embodiment, the present invention provides a method for making migrastatin and migrastatin analogs by fermentation of *Streptomyces platensis*. In a preferred embodiment, *S. platensis* strain NRRL 18993 is employed in the fermentation to produce migrastatin and migrastatin analogs.

In a second embodiment, the present invention provides a novel migrastatin analog.

In a third embodiment, the present invention provides methods for purifying migrastatin and migrastatin analogs.

In a fourth embodiment, the present invention provides pharmaceutical preparations comprising migrastatin and/or a migrastatin analog.

In a fifth embodiment, the present invention provides methods to treat cancer by administering a therapeutically effective amount of migrastatin or a migrastatin analog.

These and other embodiments, modes, and aspects of the invention are described in more detail in the following description, the examples, and claims set forth below.

DETAILED DESCRIPTION OF THE INVENTION

Migrastatin is a polyketide that inhibits the migration or movement of cells. Migrastatin has therapeutic potential in the treatment of cancer, because migrastatin can be administered, alone or in combination with other anti-cancer drugs, to prevent metastases. Unfortunately, migrastatin is quite difficult to synthesize de novo, and strains that produce the compound have heretofore either not been available or have not been identified as producers of migrastatin.

The present invention provides methods for making migrastatin, migrastatin analogs, and purified preparations of migrastatin and migrastatin analogs. In a first embodiment, the present invention provides a method for making migrastatin and migrastatin analogs by fermentation of *Streptomyces platensis*. In a preferred embodiment, *S. platensis* strain NRRL 18993 is employed in the fermentation to produce migrastatin and migrastatin analogs.

*Streptomyces platensis* NRRL 18993 has previously been identified as a source of polyketide compounds known as dorrigocins. See U.S. Pat. Nos. 5,589,485 and 5,484,799, each of which is incorporated herein by reference. Prior to the present invention, it was not known that *S. platensis* produced migrastatin. Moreover, no migrastatin analogs have been described prior to the present invention. Surprisingly, when *S. platensis* NRRL 18993 is fermented in accordance with the protocol of Example 1, below, migrastatin and a migrastatin analog are produced together with the dorrigocins known to be produced in this strain.

Migrastatin and the migrastatin analog provided by the present invention can be isolated and purified from the fermentation broth by extraction and chromatography. Examples 1 and 2, below, describe the isolation and characterization of these compounds by LC/MS. Thus, the present invention provides isolated and purified preparations of migrastatin and a novel migrastatin analog.

The present invention also provides compositions containing migrastatin or migrastatin analogs useful in the treatment of cancer and other disease conditions in which the inhibition of cell migration is beneficial.

The compounds of the invention can be readily formulated to provide the pharmaceutical compositions of the invention. The pharmaceutical compositions of the invention can be used in the form of a pharmaceutical preparation, for example, in solid, semisolid, or liquid form. This preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, *Transplantation Proceedings XIX*, Supp. 6:17–22, incorporated herein by reference. Dosage forms for external application may be prepared essentially as described in EP Pub. No. 423,714, incorporated herein by reference. The active compound is included in the pharmaceutical composition in an amount sufficient to produce the desired effect upon the disease process or condition.

For the treatment of conditions and diseases caused by infection, immune system disorder (or to suppress immune function), or cancer, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intrathecal, intramuscular, and intrasternal injection or infusion techniques.

Dosage levels of the compounds of the present invention are of the order from about 0.01 mg to about 100 mg per kilogram of body weight per day, preferably from about 0.1 mg to about 50 mg per kilogram of body weight per day. The dosage levels are useful in the treatment of the above-indicated conditions (from about 0.7 mg to about 3.5 mg per patient per day, assuming a 70 kg patient). In addition, the compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 gm of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention may be formulated within the range of, for example, 0.00001% to 60% by weight, preferably from 0.001% to 10% by weight, and most preferably from about 0.005% to 0.8% by weight.

It will be understood, however, that the specific dose level for any particlular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

In another embodiment, the present invention provides a method of treating cancer, which method comprises administering a therapeutically effective amount of migrastatin, the novel migrastatin analog compound, or both, either alone or in combination with another anti-cancer compound.

The following examples are given for the purpose of illustrating the present invention and shall not be construed as being a limitation on the scope of the invention or claims.

EXAMPLE 1

Production of Migrastatin from *Streptomyces platensis*

*Streptomyces platensis*, NRRL 18993, was obtained from the National Center for Agricultural Utilization Research. A seed flask was prepared as follows. Lyophilized cells of *S. platensis* (NRRL 18993) were put into a 250 mL baffled flask that contained 50 mL of seed medium. The flask was incubated at 28° C. on a 250 RPM shaker for 72 hours or until significant growth was observed.

A production flask was prepared as follows. About 50 mL of production medium containing Amberlite XAD-16 was sterilized in a 250 mL baffled flask. The flask was inoculated with 5% (v/v) of a seed culture. The production flask was placed in an incubator shaker operating at 250 RPM and 28° C. for 6–8 days. To harvest and extract the migrastatin compounds from the culture, the following protocol is followed.

After 6–8 days, pour contents of production flask into a 50 mL centrifuge tube. Centrifuge at ca. 3300 g for 10 minutes. Decant the supernatant without removing any XAD resin. Add 2 equal volumes of water, vortex for 5 minutes and centrifuge. Decant the water without removing any of the XAD resin. Add 2 equal volumes of methanol to the pellet and vortex until the pellet is dispersed. Place the centrifuge tube on a shaker and mix at 175 RPM for 20–30 minutes. Centrifuge the mixture for 10 minutes and save the methanol extract. Repeat the methanol extraction procedure. Combine both methanol extractions and evaporate to solids.

To prepare the migrastatin compounds for LC/MS analysis, the following protocol is followed. Add an appropriate amount of methanol to the solids so the sample is concentrated 50 times (relative to initial fermentation volume). Filter the solution using a 0.45 um PTFE filter. Transfer filtered solution to a sample vial for analysis.

| *S. platensis* Seed Medium | |
| --- | --- |
| Component | Concentration (g/L) |
| Soy Flour | 15 |
| Yeast Extract | 1 |
| NaCl | 1 |
| CaCO$_3$ | 1 |

To prepare the seed medium, combine the above components in water and bring to a final volume of 1 L. Adjust the pH to 7.0. Sterilize by autoclaving at 121° C. for 60 minutes. After the medium has cooled to room temperature, add 22 mL of a 620 g/L glucose stock solution.

| *S. platensis* Production Medium | |
| --- | --- |
| Component | Concentration (g/L) |
| Soy Flour | 20 |
| Yeast Extract | 1 |
| CaCO$_3$ | 2 |
| Amberlite XAD-16 | 100 |

To prepare the production medium, combine the above components in water and bring to a final volume of 1 L. Adjust the pH to 7.0. Sterilize by autoclaving at 121° C. for 60 minutes. After the medium has cooled to room temperature, add 29 mL of a 620 g/L glucose stock solution.

EXAMPLE 2

Detection of Migrastatin in Cultures of *Streptomyces platensis*

Migrastatin was detected in samples of cultures *Streptomyces platensis*. Identification was made by comparison of LC/MS data acquired under several conditions of cultures to an authentic standard of migrastatin. Compounds with the elemental composition of the dorrigocins, as determined by high resolution LC/MS, were also detected in the samples. Additionally, a second compound, the migrastatin analog of the invention, with a mass spectrum essentially identical to migrastatin, was also detected.

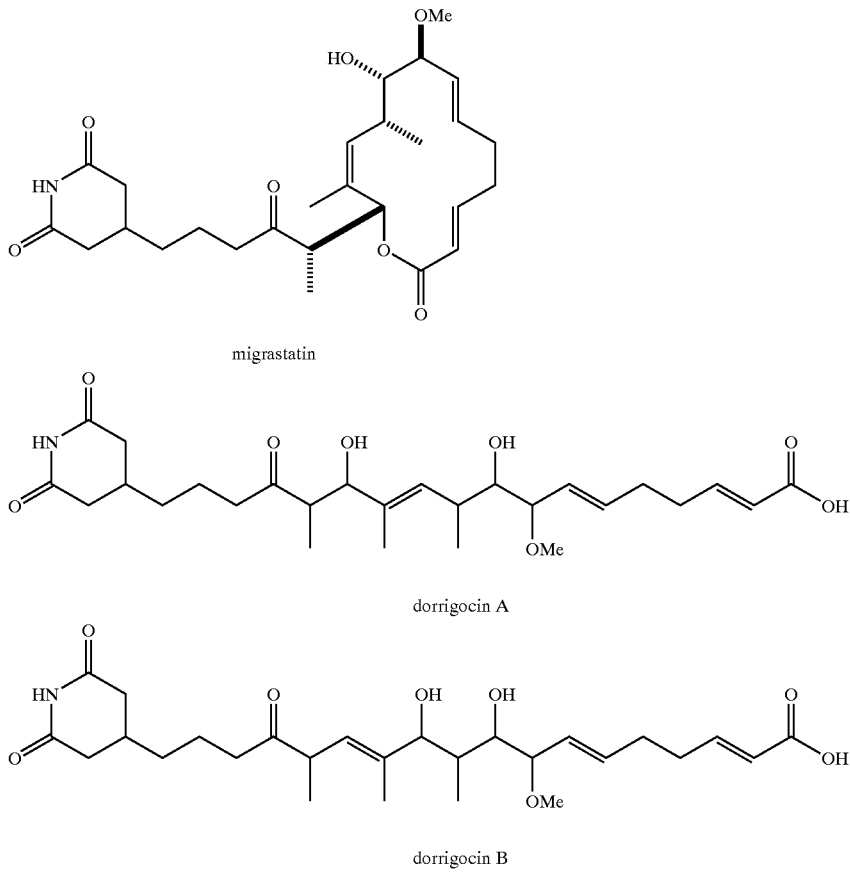

migrastatin dorrigocin A dorrigocin B

Cultures of *S. platensis* were examined for the presence of migrastatin and dorrigocins by several mass spectrometric and high-performance liquid chromatographic methods. The extracts were very complex mixtures, and the analyses were facilitated by extracted-ion chromatograms. The mass spectrum of standard migrastatin gave extensitive diagnostic fragmentation with an atmospheric pressure chemical ionization (APCI) in positive-ion mode which assisted in its identification in extracts. A compound with a mass spectrum essentially identical in fragmentation and their intensities to that of migrastatin was also detected in all samples. The ratio of migrastatin to this compound varied from sample to sample.

Attempts to minimize in-source fragmentation with either turbo-ionspray (TIS) or APCI sources in positive-ion mode on a Mariner time-of-flight mass spectrometer to get a pseudo-molecular ion signal strong enough for high resolution analysis were unsuccessful. Negative-ion mode, however, provided minimum fragmentation with the migrastatin standard and was used to acquire high resolution data on migrastatin in the extracts. High resolution data also identified two compounds with the an elemental composition consistent with them being dorrigocins.

LC/MS Conditions 1: API100LC single quadrupole LC/MS spectrometer, APCI source, positive ion mode, ring voltage 250, orifice voltage 20, source temperature 350° C. Linear gradient of 35% MeCN—H$_2$O (0.1% AcOH) to 100% MeCN (0.1% AcOH) over 8 min 1 mL/min, 4.6×150 mm Inertsil 5 µ ODS-3. Migrastatin eluted at 5.55–5.59 min under these conditions, and was detected in all samples at this retention time and identified by its distinctive mass spectrum: MS m/z 532,513 [M+Na]$^+$, 491[M+H]$^+$, 473, 458, 441, 422, 292, and 247. A second compound in all samples with a nearly identical mass spectrum eluted at 6.73–6.80 min: MS m/z 532, 513, 491, 473, 458, 441, 422, 292, and 247.

LC/MS Conditions 2: API100LC single quadrupole LC/MS spectrometer, APCI source, positive ion mode, ring voltage 250, orifice voltage 20, source temperature 350° C. Isocratic, 48% MeCN—H$_2$O (0.1 % AcOH), 1 mL/min, 4.6×150 mm Inertsil 5µ ODS-3. Migrastatin standard and in cultures eluted at 5.66–5.75 min under these conditions. The isomeric compound eluted at 10.57–10.61 min.

LC/MS Conditions 3: API100LC single quadrupole LC/MS spectrometer, APCI source, negative ion mode, ring voltage −250, orifice voltage −20, source temperature 350° C. Linear gradient of 35% MeCN—H$_2$O to 100% MeCN over 8 min, 1 mL/min, 4.6×150 mm Inertsil 5µ ODS3. Migrastatin eluted at 6.11 min. MS m/z 489 [M−H].$^-$.

LC/MS Conditions 4: Mariner time-of-flight (TOF) LC/MS spectrometer, turbo ion-spray source, negative ion mode, nozzle potential −120, source temperature 400° C., Linear gradient of 15% MeCN—H$_2$O (0.1% AcOH) to 70% MeCN (0.1% AcOH) over 12 min, 0.4 mL/min, 2.1×150 mm Inertsil 5µ ODS-3. Migrastatin eluted at 10.32–10.34 min. under these conditions and was detected in all samples analyzed. For high resolution analysis, dansyl-Gly-Trp was used as an internal mass calibrant. HRMS-TOF for m/z 488 at 10.34 min in K135-55-C1: [M−H]− calculated for $C_{27}H_{38}NO_7$ (migrastatin), 488.2643; found, 488.2628. HRMS-TOF for m/z 506 at 8.46 min: [M−H]− calculated for $C_{27}H_{40}NO_8$ (dorrigocins), 506.2748; found 506.2688. HRMS-TOF for m/z 506 at 7.97 min: [M−H]− calculated for $C_{27}H_{40}NO_8$ (dorrigocins), 506.2748; found 506.2695.

LC/MS Conditions 5: TOF LC/MS spectrometer, APCI source, positive-ion mode, nozzle potential 120, source temperature 400° C., linear gradient of 35% MeCN—$H_2O$ (0.1% AcOH) to 100% MeCN (0.1% AcOH) over 12 min, 1 mL/min, 4.6×150 mm Inertsil 5µ ODS-3.

EXAMPLE 3

Fermentation, Isolation, and Identification of Migrastatin and a Migrastatin Analog in *Streptomyces platensis*

*Streptomyces platensis* (strain NRRL 18993), a producer of dorrigocins, produces migrastatin, an inhibitor of tumor cell migration. *S. platensis* is known to produce dorrigocin A, which is structurally similar to migrastatin, differing only by a cyclization. Migrastatin was identified by TOF LC/MS and HPLC with a migrastatin standard. In accordance with the methods of the invention, product titers were improved by the addition of XAD-16 resin to the fermentation media, and purification was achieved by solid phase extraction, solid/liquid extractions, and C18 chromatography. References cited in this example are referred to by a footnote number corresponding to the number of the reference in the reference list provided below; all references cited herein are incorporated herein by reference.

Developing a treatment preventing the migration of metastatic tumor cells is essential to stopping tumor dissemination [1]. Migrastatin is a non-cytotoxic agent that has been demonstrated to inhibit tumor cell metastasis [2]. This compound was found to be more effective than clarithromycin and erythromycin against the migration of human esophageal cancer EC17 cells and mouse melanoma B16 cells [2].

While *Streptomyces platensis* is known to produce dorrigocins, it has not previously been reported as a producer of migrastatin. Migrastatin is a glutarimide antibiotic possessing a 14-membered lactone ring with a molecular formula of $C_{27}H_{39}NO_7$ [4]. Dorrigocin A is also a glutarimide antibiotic with an acyclic unsaturated ketone side chain [3,5]. In this Example, the production, purification, and identification of migrastatin and a migrastatin analog in accordance with the methods of the invention from *S. platensis* fermentation broth are described.

Materials and Methods
Strains and Culture Conditions

*Streptomyces platensis* NRRL 18993 was used for this work. Cell banks were prepared by adding glycerol (30% v/v final concentration) to a culture growing exponentially in inoculum media and then freezing 1 mL aliquots at −80° C. One cell bank vial was used to inoculate 50 mL of inoculum media in a 250 mL baffled flask. This flask was allowed to grow for 2–3 days at 250 RPM and 28° C. and then used to inoculate flask experiments containing production media at 5% of the final volume. Production flasks were run at 28° C. on a 250 rpm rotary shaker for 8 days. For fermentation studies, the 50 mL culture was transferred to 500 mL of inoculum media in a 2.8 L Fernbach flask, allowed to grow for 2 days, and used to inoculate 10 L fermenters containing production media at 5% v/v.

Inoculum cultures for the 150 L fermentor were started as described above. A 500 mL culture was subcultured into a 10 L fermentor containing inoculum media for 2 days, and then used to inoculate a 150 L fermentor containing 100 L production media at 5% v/v.

Fermentations were controlled at 28° C., pH 7.0 by addition of 2.5 N $H_2SO_4$ and 2.5 N NaOH, an agitation rate of 500–550 rpm, and an aeration rate of 0.1–0.3 VVM. Foam was controlled by the automatic addition of 50% (v/v) Antifoam B. Dissolved oxygen was controlled with agitation and aeration rate to maintain the dissolved oxygen above 50%. Cultures were harvested after 8–9 days.

Media

Inoculum media [3] consisted of 15 g/L soy flour (Giusto's Vita-Grain), 1 g/L yeast extract (Sigma), 1 g/L NaCl (Sigma), and 1 g/L $CaCO_3$ (Sigma) per liter of deionized water. The pH was adjusted to 7.0 with 2.5 N NaOH and autoclaved for 60 min at 121° C.; after cooling, sterile glucose solution (500 g/L) was added to give a final concentration of 13.6 g/L. Production media [3] contained 100 g/L XAD-16 (Amberlite), 20 g/L soy flour (Giusto's Vita-Grain), 1 g/L yeast extract (Sigma), and 2 g/L $CaCO_3$ (Sigma). The production medium pH was adjusted to 7.0 with 2.5 N NaOH and autoclaved for 60 min at 121° C.; after cooling, sterile glucose solution (500 g/L) was added to give a final concentration of 18.2 g/L.

Extraction and Analysis

About 50 ml of production culture were centrifuged at 3313 g for 10 min. The supernatant was decanted and the cell pellet with XAD was resuspended with water and centrifuged. After the water wash, 25 mL of 100 % methanol was added to the pellet and the mixture was placed on a 175 rpm shaker for 30 minutes at 30° C. The methanol was decanted and saved. The extraction was repeated, and the methanol extracts were pooled and evaporated to solids. These solids were resuspended in 2 mL of methanol for LC/MS analysis.

An API100LC single quadupole LC/MS spectrometer, with an atmospheric pressure chemical ionization (APCI) in positive-ion mode, with a ring voltage of 250, orifice voltage of 20, and a source temperature of 350° C. was used. A 4.6 mm×150 mm Inertsil 5µ ODS-3 column was used with a linear gradient from 35% Methyl Cyanide (MeCN)—$H_2O$ (0.1% acetic acid) to 100% MeCN (0.1% acetic acid) over 8 minutes at a flow rate of 1 mL/min. A migrastatin standard was provided by Dr. Haruo Seto (University of Tokyo, Tokyo, Japan).

Purification

Material purified from two 10 L fermentations was used to confirm the production of migrastatin by *S. platensis*. 1.5 L of XAD-16 resin was captured from 16 L of fermentation broth in an 8.9 cm×33 cm column and the migrastatin and a novel isomer were eluted with 10 L of 100% MeOH at a flow rate of 320 mL/min [9]. The product containing solution was evaporated to oily black solids. The solids were extracted with 250 mL of methanol and then filtered. The filtered solids were washed with an additional 50 mL of methanol. The wash and filtrate were combined and diluted with 700 mL of water. This solution was loaded onto a 4.8 cm×25 cm C18 column and eluted using a step gradient consisting of 30–100% methanol in water at a flow rate of 100 mL/min. Eight 1 L fractions were collected, and the migrastatin was found exclusively in fraction 4, which had been collected during elution with 60% methanol in water. Fraction 4 was evaporated to an oil. The oil was redissolved into 100 mL of methanol, and the total volume was brought up to 250 mL with water. The solution was loaded onto a 2.5 cm×20 cm C18 chromatography column at a flow rate of 25 mL/ min.

The column was then eluted with 40% methanol in water (800 mL, Fraction 1), 42% methanol in water (800 mL, Fraction 2), and 44% methanol in water (4 L, Fractions 3–32). Fractions 13–20 were combined and the product pool was evaporated to solids, giving an oil.

Results and Discussion

XAD Studies

Including resin in culture broth is a technique for capturing unstable molecules as well as increasing production titers in fermentations [6, 7, 8]). To address the issues of stability and titer improvement, an XAD resin study was performed examining the effects of 100, 50, 20, 10, and 5 g/L XAD-16 on titers. Although XAD-16 was used, other hydrophobic resins (e.g. HP20, Mitsubishi) demonstrated similar effects and so can be used in accordance with the methods of the inventon. About 100 g/L of XAD in the production media increased migrastatin titers 15%. Although XAD concentrations varying from about 20 g/L-about 100 g/L did not increase production of migrastatin, these concentrations did increase production of a novel isomer provided by the invention (isomigrastatin) found in fermentation broth, and 100 g/L was used. Binding to resin may provide a stabilizing effect to migrastatin [3, 6]). Migrastatin or its novel isomer may be toxic to the cells above a certain level, and thus removing migrastatin or isomigrastatin from the broth and onto resin can increase titers [6]). XAD-16 may also bind certain nutrients in the fermentation broth and thus influence secondary metabolism [6]).

Fermentation

A series of shake flask studies were completed to determine whether the strain *S. platensis* (NRRL 18993) produced migrastatin. After detecting migrastatin in shake flasks, the process was scaled up to the 10 L scale and then to the 150 L scale to produce more material for confirmation as well as further studies. In the process of detecting migrastatin, an isomer was also found. The isomer was the major product in the 150 L fermentation, accumulating three times as much as migrastatin. Production of migrastatin peaked on day 7 in the 150 L fermentation. The culture was harvested from the 150 L fermentation on day 9.

Purification

The purification process used for migrastatin and provided by the present invention involves solid phase extraction of the fermentation broth, followed by methanol extraction, two C18 chromatography fractionation steps, and acetone extraction. Purity after solid phase extraction and C18 fractionation was 0.43% and 11% respectively. Final product purity after the acetone extraction was 94%, and overall recovery of the migrastatin was 76%.

Detection and Identification

Cultures of *S. platensis* were examined for the presence of migrastatin and dorrigocins by several mass spectrometric and high-performance liquid chromatographic methods. NMR was also used on the compound. The mass spectrum of standard migrastatin gave extensive diagnostic fragmentation with APCI in positive-ion mode, which assisted in its identification in extracts. Negative ion mode provided minimum fragmentation with the migrastatin standard and was used to acquire high-resolution data on the migrastatin in the broth. High-resolution data also identified two compounds with an elemental composition consistent with dorrigocins [9]). Additionally, a compound with a mass spectrum essentially identical to migrastatin, called "isomigrastatin", was also detected. Migrastatin eluted at 5.55–5.59 min and was identified by its distinctive mass spectrum: MS m/z 532, 513, 491, 473, 458, 441, 422,292, and 247. The isomer eluted at 6.73–6.80 min and was identified by MS m/z 532, 513, 491, 473, 458, 441, 422, 292, and 247.

Thus, in addition to dorrigocin, *Streptomyces platensis* also produces migrastatin and isomigrastatin. Production of migrastatin peaked after 7 days. XAD-16 was used to improve titers as well as stabilize the molecule. LC/MS and NMR were done on purified material (94% purity) to identify and confirm the structure of migrastatin from fermentation media and extracts against a migrastatin standard. LC/MS also detected an isomer of migrastatin.

References

1. Woodhouse, E. C.; R. F. Chuaqui & L. A. Liotta: General Mechanism of metastasis. Cancer 80:1529~1537, 1997
2. Nakae K.; Y. Yoshimoto, T. Sawa, Y. Homma, M. Hamada, T. Takeuchi, & M. Imoto. Migrastatin, a new inhibitor of tumor cell migration from Streptomyces sp. MK929–43F1. Taxonomy, fermentation, isolation and biological activities. J. Antibiotics (Tokyo) 53:1130~1136, 2000
3. Karwowski J. P.; M. Jackson, G. Sunga, P. Sheldon, J. B. Poddig, W. L. Kohl, & S. Kadam. Dorrigocins: novel antifungal antibiotics that change the morphology of ras-transformed NIH/3T3 cells to that of normal cells. I. Taxonomy of the producing organism, fermentation, and biological activity. J. Antibiotics 47:862~869, 1994
4. Nakae K.; Y. Yoshimoto, M. Ueda, S. Tsutomu, Y. Takahashi, H. Naganawa, T. Takeuchi, & M. Imoto. Migrastatin, a novel 14-membered lactone from Streptomyces sp. MK92943F1. J of Antibiotics (Tokyo) 53:1228~1230, 2000
5. Kadam S. & J. B. McAlpine. Dorrigocins: novel antifungal antibiotics that change the morphology of ras-transformed NIH/3T3 cells to that of normal cells. III Biological properties and mechanism of action. J. Antibiotics 47:875~880, 1994
6. Jarvis, B. B.; C. A. Armstrong, & M. Zeng. Use of resins for trichothecene production in liquid cultures. J. Antibiotics 43:1502~1504, 1990
7. Warr G. A.; J. A. Veitch, A. W. Walsh, G. A. Hesler, D. M. Pirnik, J. E. Leet, P. M. Lin, I. A. Medina, K. D. McBrien, S. Forenza, J. M. Clark, & K. S. Lam. BMS-182123, a fungal metabolite that inhibits the production of TNF-α by macrophages and monocytes. J. Antibiotics 49:234 ~240, 1996
8. Marshall V. P.; S. J. McWethy, J. M. Sirotti, & J. O. Cialdella. The effect of neutral resins on the fermentation production of rubadirin. J. Industrial Microbiology 5:283~288, 1990
9. Hochlowski, J. E.; D. N. Whittern, P. Hill, & J. B. McAlpine. Dorrigocins: novel antifungal antibiotics that change the morphology of ras-transformed NIH/3T3 cells to that of normal cells. II. Isolation and elucidation of structure. J. Antibiotics 47:870~874, 1994

The invention having now been described by way of written description and examples, those of skill in the art will recognize that the invention can be practiced in a variety of embodiments and that the foregoing description and examples are for purposes of illustration and not limitation of the following claims.

What is claimed is:

1. A method for producing migrastatin comprising
   a) fermenting *Streptomyces platensis* in a medium under conditions such that migrastatin is produced and,
   b) purifying migrastatin from the medium.

2. The method of claim 1, wherein said *Streptomyces platensis* is NRRL 18993.

3. The method of claim 2, wherein migrastatin is purified by a method comprising (1) solid phase extraction; (2) extraction with an organic solvent, and (3) chromatography.

4. The method of claim 3, wherein migrastatin is purified by a method comprising (1) solid phase extraction; (2) extraction with methanol, (3) chromatography with C18 resin; and (4) extraction with acetone.

5. The method of claim 1, wherein said fermentation is conducted in a medium comprising a resin that binds migrastatin.

6. The method of claim 5, wherein said resin is XAD resin.

7. The method of claim 6, wherein migrastatin is purified by a method comprising (1) solid phase extraction; (2) extraction with an organic solvent, and (3) chromatography.

8. The method of claim 7, wherein migrastatin is purified by a method comprising (1) solid phase extraction; (2) extraction with methanol, (3) chromatography with C18 resin; and (4) extraction with acetone.

9. The method of claim 1, wherein migrastatin is purified by a method comprising (1) solid phase extraction; (2) extraction with an organic solvent, and (3) chromatography.

10. The method of claim 9, wherein migrastatin is purified by a method comprising (1) solid phase extraction; (2) extraction with methanol, (3) chromatography with C18 resin; and (4) extraction with acetone.

* * * * *